United States Patent [19]

Cooper et al.

[11] Patent Number: 5,298,522
[45] Date of Patent: Mar. 29, 1994

[54] 6-CHLORO-5-FLUORO-3-(2-THENOYL)-2-OXINDOLE-1-CARBOXAMIDE AS AN ANALGESIC AND ANTI-INFLAMMATORY AGENT WHILE MAINTAINING A NORMAL URINE PROTEIN/CREATININE RATIO

[75] Inventors: Kelvin Cooper, Nonak; Bruce H. Littman, Stonington; Christopher J. Pazoles, Waterford; Keith D. Wilner, Groton, all of Conn.

[73] Assignee: Pfizer Inc., New York, N.Y.

[21] Appl. No.: 7,217

[22] Filed: Jan. 22, 1993

[51] Int. Cl.$^5$ ............................................. A61K 31/40
[52] U.S. Cl. ............................................. 514/414
[58] Field of Search ............................................. 514/414

[56] References Cited

U.S. PATENT DOCUMENTS

| | | | |
|---|---|---|---|
| 4,556,672 | 12/1985 | Kadin | 514/414 |
| 4,569,942 | 2/1986 | Kadin | 514/414 |
| 4,658,037 | 4/1987 | Kadin | 514/414 |
| 4,853,409 | 8/1989 | Showell | 514/414 |
| 4,861,794 | 8/1989 | Otterness | 514/44 |
| 5,047,554 | 9/1991 | Ehrgott | 514/414 |

*Primary Examiner*—S. J. Friedman
*Attorney, Agent, or Firm*—Peter C. Richardson; Gregg C. Benson; Mervin E. Brokke

[57] ABSTRACT

A method of producing analgesia and treating antiinflammatory disease in a human subject while avoiding proteinuria by administering 6-chloro-5-fluoro-3-(2-thenoyl)-2-oxindole-1-carboxamide or a pharmaceutically-acceptable base salt thereof.

1 Claim, No Drawings

6-CHLORO-5-FLUORO-3-(2-THENOYL)-2-OXINDOLE-1-CARBOXAMIDE AS AN ANALGESIC AND ANTI-INFLAMMATORY AGENT WHILE MAINTAINING A NORMAL URINE PROTEIN/CREATININE RATIO

This invention relates to a method of producing analgesia and a method of treating an inflammatory disease in a human subject without inducing proteinuria.

BACKGROUND OF THE INVENTION

Kadin in U.S. Pat. No. 4,556,672 describes certain 2-oxindole-1-carboxamide compounds with acyl substituents at the 3-position which are inhibitors of cyclooxygenase (CO) and lipoxygenase (LO) enzymes. These compounds are useful as analgesic agents in mammals and are useful in ameliorating or eliminating pain, such as pain experienced by patients recovering from surgery or trauma. These compounds are also useful for chronic administration to mammals to alleviate the symptoms of chronic diseases such as the inflammation and pain associated with rheumatoid arthritis and osteoarthritis. Kadin specifically claims a method of eliciting an analgesic response, and also a method of treating an inflammatory disease, in a mammalian subject, which comprises treating said mammalian subject with an effective amount of member selected from a genus of 2-oxindole-1-carboxamides. This genus includes the chemical compound 6-chloro-5-fluoro-3-(2-thenoyl)-2-oxindole-1-carboxamide. However, use of this latter compound is not specifically identified. The 2-oxindole-1-carboxamides of Kadin are highly effective analgesics and antiinflammatories; but 5-chloro-3-(2-thenoyl)-2-oxindole-1-carboxamide in this group of compounds has been found to induce non-progressive, reversible proteinuria in some patients. 6-Chloro-5-fluoro-3-(2-thenoyl)-2-oxindole-1-carboxamide does not induce proteinuria.

SUMMARY OF THE INVENTION

This invention provides an improved method of eliciting an analgesic or antiinflammatory response in a human subject by administering to said human subject an effective analgesic or antiinflammatory amount of a 3-acyl-2-oxindole-1-carboxamide compound, in which the improvement comprises eliciting such analgesic or antiinflammatory response while maintaining a normal urine protein/creatinine ratio in said subject by administering an analgesic or antiinflammatory, and non-proteinuric eliciting amount of 6-chloro-5-fluoro-3-(2-thenoyl)-2-oxindole-1-carboxamide or a pharmaceutically acceptable base salt thereof.

DETAILED DESCRIPTION OF THE INVENTION

6-Chloro-5-fluoro-3-(2-thenoyl)-2-oxindole-1-carboxamide (I) is prepared by the following sequence of reactions as described in U.S. Pat. No. 4,556,672 herein incorporated by reference and preparations 1-3.

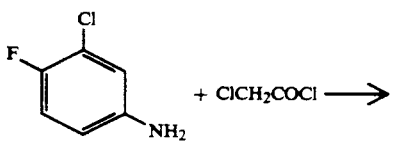

II

-continued

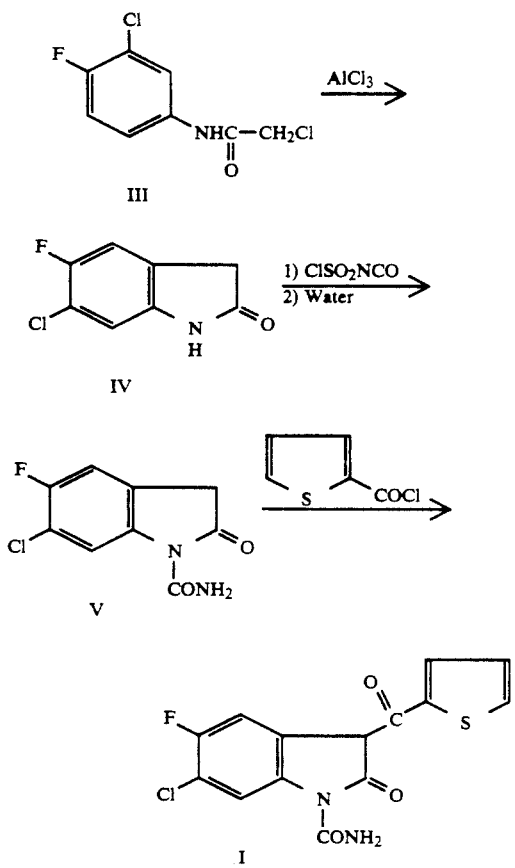

6-Chloro-5-fluoro-3-(2-thenoyl)-2-oxindole-1-carboxamide is acidic and forms base salts. All such base salts are within the scope of this invention and they can be prepared by conventional methods. For example, they can be prepared simply by combining the acidic and basic entities, usually in a stoichiometric ratio, in either an aqueous, non-aqueous or partially aqueous medium, as appropriate, or by interconverting one salt with another salt. The salts are recovered either by filtration, by precipitation with another solvent followed by filtration, by evaporation of the solvent, as appropriate, or, in the case of aqueous solutions, by lyophilization. Preferred salts are those of esters of naturally occurring amino acids.

6-Chloro-5-fluoro-3-(2-thenoyl)-2-oxindole-1-carboxamide is recognized to exist in a number of enolic forms, all such tautomers are within the scope of this invention.

"Significant increase or decrease" for proteinuria effects is herein defined as an increase or decrease having statistical significance as determined by conducting an analysis of variance (ANOVA). First, a regression line is fitted to protein/creatinine (PC) ratio data for each patient and treatment period, and a slope is determined. The slope is then analyzed using an ANOVA to test for sequence, period and treatment effects, to determine if a difference exists between the control and treated groups.

6-Chloro-5-fluoro-3-(2-thenoyl)-2-oxindole-1-carboxamide and salts thereof possess analgesic activity. This activity can be demonstrated in mice by showing blockage of the abdominal stretching induced by administration of 2-phenyl-1,4-benzoquinone (PBQ). The method is based on that of Siegmund et al., *Proc. Soc. Exp. Biol. Med.*, 95, 729–731, (1957), as adapted for high throughput [see further Milne and Twomey, *Agents and Actions*, 10, 31–37, (1980)]. The mice used in these experiments are Carworth males, albino CF-1 strain, weighing 18–20 g. All mice are fasted overnight prior to drug administration and testing.

6-Chloro-5-fluoro-3-(2-thenoyl)-2-oxindole-1-carboxamide is dissolved or suspended in a vehicle consisting of ethanol (5%), emulphor 620 (a mixture of polyoxyethylene fatty acid esters, 5%) and saline (90%). This vehicle also served as control. Doses are on a logarithmic scale (i.e., ... 0.32, 1.0, 3.2, 10.32 ... mg/kg), and are calculated from weights of the salt when applicable. The route of administration is oral, with concentrations varied to allow a constant dosage of 10 ml/kg of mouse. The aforesaid method of Milne and Towney is used to determine efficacy and potency. Mice are treated with compounds orally, and one hour later received PBQ, 2 mg/kg intraperitoneally. Individual mice are then immediately placed in a warmed lucite chamber, and, starting five minutes after PBQ administration, the number of abdominal constrictions during the subsequent 5 minutes are recorded. The degree of analgesic protection, Maximal Possible Effect (% MPE), is calculated on the basis of suppression of abdominal constriction relative to counts from concurrent control animals run on the same day. At least four such determinations provide dose-response data for generation of an $MPE_{50}$, the best estimate of the dose that reduces abdominal constriction to 50% of control levels.

6-Chloro-5-fluoro-3-(2-thenoyl)-2-oxindole-1-carboxamide also possesses anti-inflammatory activity. This activity can be demonstrated in rats by a method based on the standard carrageenin-induced rat-foot edema test. [Winter et al., *Proc. Soc. Exp. Biol. Med.*, 111, 544, (1963)].

Unanesthetized, adult, male, albino rats of 150 g to 190 g body weight are numbered, weighed, and an ink mark placed on the right lateral malleolus. Each paw is immersed in mercury exactly to the ink mark. The mercury is contained in a glass cylinder, connected to a Statham Pressure Transducer. The output from the transducer is fed through a control unit to a microvoltameter. The volume of mercury displaced by the immersed paw is read. The drug is given by gavage. One hour after drug administration, edema is induced by injection of 0.05 ml of 1% solution of carrageenin into the plantar tissue of the marked paws. Immediately thereafter, the volume of the injected foot is measured. The increase in foot volume 3 hours after the injection of carrageenin constitutes the individual inflammatory response.

The analgesic activity of 6-chloro-5-fluoro-3-(2-thenoyl)-2-oxindole-1-carboxamide and salts thereof make them useful for acute administration to mammals for the control of pain, e.g., post-operative pain and the pain of trauma. Additionally 6-chloro-5-fluoro-3-(2-thenoyl)-2-oxindole-1-carboxamide is useful for chronic administration to mammals for the alleviation of the symptoms of chronic diseases, such as the inflammation of rheumatoid arthritis, and the pain associated with inflammation in osteoarthritis and other musculoskeletal and inflammatory disorders.

Large amounts of creatinine and much smaller amounts of protein are normally excreted in the urine of normal human subjects, and a protein/creatinine ratio of approximately 0.05 to 0.1 is usually maintained. A normal urine protein/creatinine ratio is herein defined as the protein/creatinine ratio exhibited by the subject prior to administration of any medication. A "non-proteinuria eliciting amount" is herein defined as a dosage of an analgesic or antiinflammatory compound which does not significantly increase the urine protein/creatinine ratio of the subject over the normal value.

5-Chloro-3-(2-thenoyl)-2-oxindole-1-carboxamide has been found to cause proteinuria in 10–15% of patients within four weeks at 80 mg/day; the proteinurea is non-progressive and reversible upon discontinuation of medication. The compound of this invention does not cause proteinuria at 320 mg/day. See Examples 1 and 2.

When 6-chloro-5-fluoro-3-(2-thenoyl)-2-oxindole-1-carboxamide or a pharmaceutically acceptable salt thereof is to be used as either an analgesic agent or an anti-inflammatory agent, it can be administered to a human subject either alone, or, preferably, in combination with pharmaceutically-acceptable carriers or diluents in a pharmaceutical composition, according to standard pharmaceutical practice. The compound can be administered orally or parenterally. Parenteral administration includes intravenous, intramuscular, intraperitoneal, subcutaneous and topical administration.

In a pharmaceutical composition comprising 6-chloro-5-fluoro-3-(2-thenoyl)-2-oxindole-1-carboxamide, or a pharmaceutically-acceptable salt thereof the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of 6-chloro-5-fluoro-3-(2-thenoyl)-2-oxindole-1-carboxamide, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When 6-chloro-5-fluoro-3-(2-thenoyl)-2-oxindole-1-carboxamide or salt thereof is used in a human subject, the daily dosage will normally be determined by the prescribing physician. Moreover, the dosage will vary according to the age, weight and response of the individual patient, as well as the severity of the patient's symptoms and the potency of the particular formulation being administered. However, for acute administration to relieve pain, an effective dose in most instances will be 0.01 to 0.5 g as needed (e.g., every four to six hours). For chronic administration, in most instances an effective dose will be from 0.01 to 1.0 g per day, and preferably 1 to 320 mg per day and more preferably 40 to 160 mg per day, in single or divided doses. On the other hand, it may be necessary to use dosages outside these limits in some cases.

The following examples and preparations are being provided solely for the purpose of further illustration.

EXAMPLE 1

Using a double blind placebo-controlled design, 6-chloro-5-fluoro-3-(2-thenoyl)-2-oxindole-1-carboxamide was administered to 36 patients at dose levels of 40, 80, 160 and 320 mg, once daily. A single dose was given on day 1, followed by a seven day washout period, and then dosing was continued for a further 21 days. At each dose level, nine subjects received 6-chloro-5-fluoro-3-(thenoyl)-2-oxindole-1-carboxamide and three subjects received placebo, with the placebo given as an identical matching form. The study was double blind with respect to within group assignment and single blind with respect to between group assignment. Computer generated randomization was used to assign subjects to the various treatment regimens. Each dose (drug and placebo) was administered after an overnight fast with 240 ml of water. On the first and last day of dosing, blood sufficient for 1 ml plasma was collected at hour 0 (for baseline) and 0.5, 1, 2, 3, 4, 6, 8, 12, 16, 24, 48, 72, 96, 120, 144 and 168 hours postdose (for the last day of dosing 192, 216 and 240 hour samples were also collected). Urine (24 hr) was also collected on the first and last day of dosing for the determination of creatinine, uric acid, $\beta$2-microglobulin, albumin and total protein. In addition, following the 2nd, 8th and 22nd dose; and 240 hours after the last dose, one 20 ml aliquot of urine, following the first am void but prior to the administration of study medication, was withdrawn for measurement of quantitative protein and creatinine. Throughout these studies, there were no significant differences in the urine protein/creatinine ratios between the drug treated groups and the placebo treated groups.

EXAMPLE 2

Using a double blind, placebo controlled, crossover design, 6-chloro-5-fluoro-3-(2-thenoyl)-2-oxindole-1-carboxamide was administered to 25 patients at a dose level of 80 mg/day. Patients were randomized to receive either 6-chloro-5-fluoro-3-(2-thenoyl)-2-oxindole-1-carboxamide for four weeks followed by placebo for four weeks, or to receive placebo for four weeks followed by 6-chloro-5-fluoro-3-(2-thenoyl)-2-oxindole-1-carboxamide for four weeks. Patients could switch to the second leg of the treatment regimen earlier if symptoms became intolerable. Before starting treatment all existing non-steroidal antiinflammatory medication was stopped and a washout period of one week implemented. Urine protein/creatinine ratio was determined at baseline and weekly during the study. The protocol required 24 hour urine collections to confirm any increase in estimated 24 hour protein excretion based on the protein/creatinine ratios. No significant changes in the urine protein/creatinine ratio was observed during 6-chloro-5-fluoro-3-(2-thenoyl)-2-oxindole-1-carboxamide treatment and no significant differences between the protein/creatinine ratio during 6-chloro-5-fluoro-3-(2-thenoyl)-2-oxindole-1-carboxamide and placebo treatment were seen.

PREPARATION 1

6-Chloro-5-fluoro-2-oxindole

To 130 ml of toluene was added, with stirring, 24.0 g (0.165 mole) of 3-chloro-4-fluoroaniline and 13.5 ml (0.166 mole) of pyridine. The resulting solution was cooled to ca. 0° C. and 13.2 ml (0.166 mole) of 2-chloroacetyl chloride was added. The reaction mixture was stirred at room temperature for 5 hours and then it was extracted twice with 100 ml of 1N hydrochloric acid, followed by 100 ml of saturated sodium chloride solution. The resulting toluene solution was dried using magnesium sulfate, and then it was concentrated in vacuo to give 32.6 g (88% yield) of N-(2-chloroactey1)-3-chloro-4-fluoroaniline.

A 26.63 g sample of the N-(2-chloroacetyl)-3-chloro-4-fluoroaniline was thoroughly mixed with 64 g of anhydrous aluminum chloride, and the mixture was heated at 210°-230° C. for 8.5 hours. The reaction mixture was then poured onto a mixture of ice and 1N hydrochloric acid, with stirring. Stirring was continued for 30 minutes, and then the solid was collected by filtration (22.0 g). The solid was dissolved in 1:1 ethyl acetate-hexane and chromatographed on 800 g of silica gel. Elution of the column, followed by evaporation of the fractions, produced 11.7 g of the N-(2-chloroacetyl)-3-chloro-4-fluoroaniline, followed by 3.0 g of 6-chloro-5-fluoro-2-oxindole. The latter material was recrystallized from toluene to give 1.70 g (7% yield) of the title compound, m.p. 196°-206° C. Analysis by NMR spectroscopy indicated that the product was contaminated by some 4-chloro-5-fluoro-2-oxindole.

PREPARATION 2

6-Chloro-5-fluoro-2-oxindole-1-carboxamide

To a slurry of 6-chloro-5-fluoro-2-oxindole (0.04 mole) in acetonitrile (80 ml) was added chlorosulfonyl isocyanate (6.65 g, 0.047 mole) and the mixture was stirred for 45 minutes. Water (100 ml) was then added and the aqueous mixture was stirred for one hour. The precipitate which formed was filtered off and recrystallized from acetonitrile to give 0.92 g of the title product. Extraction of the filtrate from the aqueous reaction mixture with ethyl acetate (300 ml) followed by drying the extract over $MgSO_4$ and then evaporating it under reduced pressure gave additional product. Recrystallization from acetonitrile gave an additional 2.2 g of product, m.p. 229°-231° C.

PREPARATION 3

6-Chloro-5-fluoro-3-(2-thenoyl)-2-oxindole-1-carboxamide

A stirred slurry of 0.1 mole of 6-chloro-5-fluoro-oxindole-2-carboxamide and 26.9 g (0.22 mole) of 4-(N,N-dimethylamino)pyridine in 200 ml of N,N-dimethylformamide was cooled to ice-bath temperature, and then a solution of 16.1 g (0.11 mole) of 2-thenoyl chloride in 50 ml of N,N-dimethylformamide was added dropwise. Stirring was continued for ca. 30 minutes and then the reaction mixture was poured into a mixture of 1 liter of water and 75 ml of 3N hydrochloric acid. The resulting mixture was cooled in an ice-bath, and then the solid was collected by filtration. The solid was washed with water and then recrystallized from 1800 ml of acetic acid, to give 26.6 g of the title compound as fluffy, yellow crystals, m.p. 220°-221° C.

We claim:

1. A method of eliciting an analgesic or anti-inflammatory response while maintaining a normal urine protein/creatinine ratio in a human subject suffering from pain or inflammatory condition, which human subject is susceptible to non-progressive, reversible proteinuria induced by 2-oxindole-1-carboxamide analgesics and antiinflammatories, which comprises administering to said human subject an effective analgesic or antiinflammatory and non-proteinuria eliciting amount of 6-chloro-5-fluoro-3-(2-thenoyl)-2-oxindole-1-carboxamide or a pharmaceutically accept-able base salt thereof.

* * * * *